(12) United States Patent
Heerah et al.

(10) Patent No.: US 9,498,181 B2
(45) Date of Patent: Nov. 22, 2016

(54) SENSOR AND STETHOSCOPE

(71) Applicant: Computerized Medical Technology in Sweden AB, Hallsta (SE)

(72) Inventors: Aditya Heerah, London (GB); Magnus Sörlander, La Jolla, CA (US)

(73) Assignee: COMPUTERIZED MEDICAL TECHNOLOGY IN SWEDEN AB, Hallsta (SE)

( * ) Notice: Subject to any disclaimer, the term of this patent is extended or adjusted under 35 U.S.C. 154(b) by 0 days.

(21) Appl. No.: 14/383,037

(22) PCT Filed: Mar. 7, 2013

(86) PCT No.: PCT/EP2013/054615
§ 371 (c)(1),
(2) Date: Sep. 4, 2014

(87) PCT Pub. No.: WO2013/132012
PCT Pub. Date: Sep. 12, 2013

(65) Prior Publication Data
US 2015/0051511 A1     Feb. 19, 2015

Related U.S. Application Data

(60) Provisional application No. 61/607,850, filed on Mar. 7, 2012.

(51) Int. Cl.
*H01L 41/113* (2006.01)
*A61B 7/04* (2006.01)

(52) U.S. Cl.
CPC ............ *A61B 7/04* (2013.01); *H01L 41/1132* (2013.01); *A61B 2562/0204* (2013.01)

(58) Field of Classification Search
CPC .......................... H01L 41/113; H01L 41/1132
USPC ................................ 310/329–332, 338, 339
See application file for complete search history.

(56) References Cited

U.S. PATENT DOCUMENTS 2,193,945 A * 3/1940 Weisglass ............. A61B 5/022
                                                                137/551
2,564,562 A * 8/1951 Chess ....................... H04R 1/42
                                                                310/334

(Continued)

FOREIGN PATENT DOCUMENTS

| DE | 750602 C | 1/1945 |
|---|---|---|
| JP | 6-508498 | 9/1994 |
| JP | 2006-263476 A | 10/2006 |
| JP | 2011-97311 A | 5/2011 |
| JP | 2012-127759 A | 7/2012 |
| WO | 9953277 A1 | 10/1999 |

OTHER PUBLICATIONS

Chinese Office Action Dated Aug. 27, 2015 with English Translation.

(Continued)

*Primary Examiner* — Derek Rosenau
(74) *Attorney, Agent, or Firm* — Park, Vaughan, Fleming & Dowler LLP (57) ABSTRACT

It is presented a sensor comprising a sensor plate (14), a base piece (15) and a first sensor membrane (7*a*) and a second sensor membrane (7*b*), each having a side of positive electrical polarity and a side of negative electrical polarity. Each one of the first sensor membrane and the second sensor membrane is mounted between the sensor plate and the base piece while allowing movement of the sensor plate in relation to the mounting piece. The first sensor membrane and the second sensor membrane are mounted such that their respective sides of positive electrical polarity face each other or face away from each other. A corresponding electronic stethoscope is also presented.

16 Claims, 6 Drawing Sheets

(56) References Cited

U.S. PATENT DOCUMENTS

| | | | |
|---|---|---|---|
| 3,947,644 A | 3/1976 | Uchikawa | |
| 6,215,225 B1* | 4/2001 | Ishikawa et al. | 310/319 |
| 2008/0136292 A1* | 6/2008 | Thiesen | 310/334 |
| 2008/0150396 A1* | 6/2008 | Clingman et al. | 310/331 |

OTHER PUBLICATIONS

Japanese Office Action from corresponding Japanese Patent application No. 2014-560376, Dispatch Number: 129923, Dispatch Date Mar. 24, 2015. In Japanese with English translation.

* cited by examiner

SENSOR AND STETHOSCOPE

TECHNICAL FIELD

The invention relates to a sensor and an electronic stethoscope comprising such a sensor.

BACKGROUND

Sensors and transducers are manufactured to fulfil a specific sensing role and their design is optimized for the given application. For example, sensors can be arranged to detect a force or a change in force, e.g. due to a vibration, sound etc.

There is always a need to improve desired sensor signals and/or reduce the effect of undesired sensor signals,

SUMMARY

It is an object to reduce unwanted signals from sensors comprising sensor membranes.

According to one aspect, it is presented a sensor comprising: a sensor plate; a base piece; and a first sensor membrane and a second sensor membrane, each having a side of positive electrical polarity and a side of negative electrical polarity. Each one of the first sensor membrane and the second sensor membrane is mounted between the sensor plate and the base piece while allowing movement of the sensor plate in relation to the mounting piece; and the first sensor membrane and the second sensor membrane are mounted such that their respective sides of positive electrical polarity face each other or face away from each other.

Each sensor membrane may be is a force sensitive membrane.

Each sensor membrane may be configured to generate a sensor signal based on force components perpendicular to a plane of the sensor membrane along a side of the sensor membrane.

The first sensor membrane and the second sensor membrane may be mounted such that their respective sides of negative electrical polarity face each other or face away from each other.

The sensor may further comprise a third sensor membrane and a fourth sensor membrane, each having a side of positive electrical polarity and a side of negative electrical polarity. In this case, each one of the third sensor membrane and the fourth sensor membrane is mounted between the sensor plate and the base piece while allowing movement of the sensor plate in relation to the mounting piece; and the third sensor membrane and the fourth sensor membrane are mounted such that their respective sides of positive electrical polarity face each other or face away from each other.

The sensor membranes may be arranged such that a planar movement of the sensor plate, in relation to the base piece, is more restricted in a first direction along the sensor plate compared to a second direction along the sensor plate.

Each one of the third sensor membrane and the fourth sensor membrane may be longer than each one of the first sensor membrane and the second sensor membrane, measured along the respective sensor membrane between the sensor plate and the base piece. In this way, the third sensor membrane and the fourth sensor membrane are curved more than the first sensor membrane and the second sensor membrane The shortest line between the first sensor membrane and the second sensor membrane may be essentially perpendicular to the shortest line between the third sensor membrane and the fourth sensor membrane. Essentially perpendicular can here be interpreted as a deviation of less than 30 degrees from 90 degrees. In one embodiment, essentially perpendicular is to be interpreted as a deviation of less than 10 degrees from 90 degrees.

The shortest line between the first sensor membrane and the second sensor membrane may be essentially parallel to the shortest line between the third sensor membrane and the fourth sensor membrane.

The sensor may further comprise a fifth sensor membrane and a sixth sensor membrane of the same type as the other sensor membranes, the fifth sensor membrane and sixth sensor membrane being mounted between the base piece and the sensor plate such that the shortest line between the fifth sensor membrane and the sixth sensor membrane is essentially parallel to the shortest line between the third sensor membrane and the fourth sensor membrane.

The first sensor membrane and the second sensor membrane may have a first stiffness and the third sensor membrane and the second sensor membrane may have a second stiffness which differs from the first stiffness.

The sensor may further comprise a combiner which combines signals from each one of the sensor membranes to a combined signal output.

The combiner may be a summing amplifier.

Each one of the sensor membranes may comprise a piezoelectric film.

The sensor may further comprise a dampener arranged between the base plate and the sensor plate.

According to a second aspect, it is presented an electronic stethoscope comprising a sensor according to any one of the preceding claims.

Generally, all terms used in the claims are to be interpreted according to their ordinary meaning in the technical field, unless explicitly defined otherwise herein. All references to "a/an/the element, apparatus, component, means, step, etc." are to be interpreted openly as referring to at least one instance of the element, apparatus, component, means, step, etc., unless explicitly stated otherwise. The steps of any method disclosed herein do not have to be performed in the exact order disclosed, unless explicitly stated.

BRIEF DESCRIPTION OF THE DRAWINGS

The invention is now described, by way of example, with reference to the accompanying drawings, in which.

DETAILED DESCRIPTION

The invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout the description.

Figure 1A:
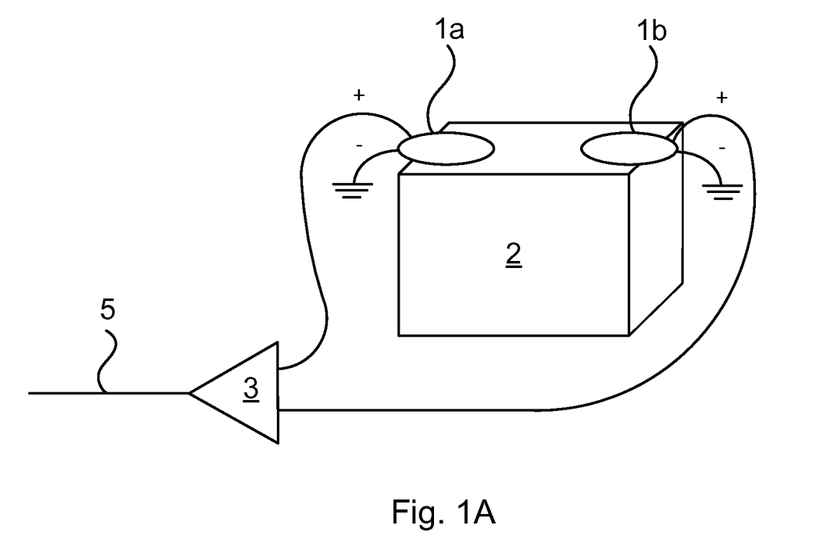
FIGS. 1A-B are schematic diagrams showing a general application of multiple sensors.
Figure 1B:
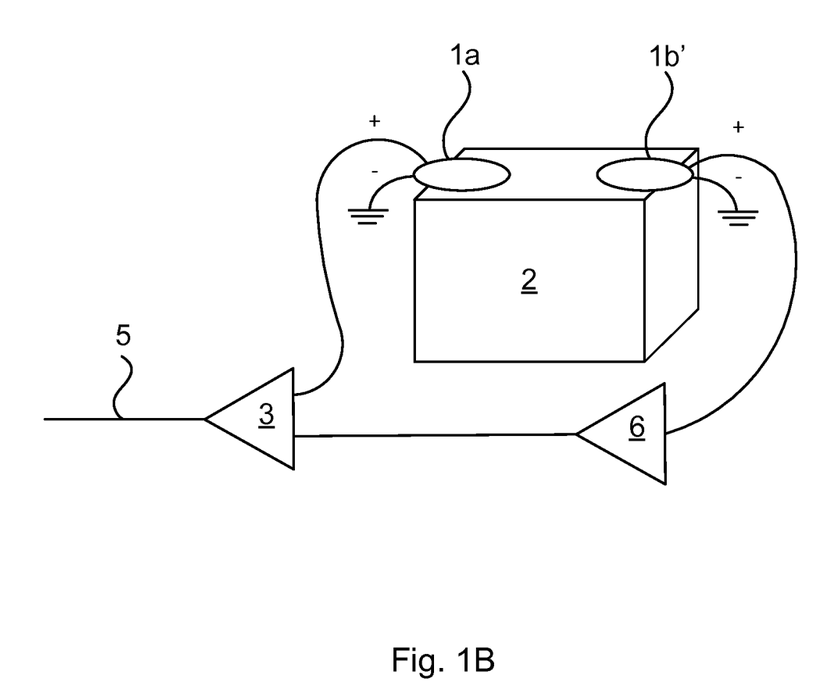

FIGS. 1A-B are schematic diagrams showing a general application of multiple sensors. In FIG. 1A, there is a first sensor 1a and a second sensor 1b arranged to detect some parameter of an object under test 2. The parameter can e.g. be force variations, such as vibrations within and/or outside a frequency range which is audible for humans. The object under test 2 can e.g. be a person or other object. The signals from the two sensors 1a-b are combined and added in a combiner 3 such as a summing amplifier and provided to a combined signal output 5. When a summing amplifier is used as a combiner, electronic noise generated by high gain amplification can be reduced. In FIG. 1A, the two sensors 1A-B are arranged such that the output of the two sensors are added on top of each other.

In FIG. 1B, there is an inverting amplifier 6 between one of the sensors (in this example the second sensor 1b) and the summing amplifier 3. Hence, the two sensors are combined in opposition with regards to the polarity of their output. In this case, the electronics 6 employed inverts the signals from the sensors in opposition prior to summation. This scenario is beneficial in situations where common mode electrical noise occurs in each sensor path. I.e. if the sensor configuration is prone to hum pick up, then hum cancellation will occur when signals are inverted and then summed. In certain situations a sensor is mounted to, or situated in, a secondary housing and steps may then be taken reduce unwanted pickup. For example a microphone may have its sensing element shock mounted with elastic or rubber. Though it is not a contact sensor the microphone illustrates the point.

Principle Behind Rejection of Undesired Signals

Embodiments presented herein comprise sensors in one or more pairs. Each pair contains sensors mounted in electrical opposition. The sensor membranes can comprise piezoelectric film, piezo-resistive material or similar sensor membrane. One pair will give reduction of unwanted signals for one plane of movement and two pairs can be employed for sensing on a preferential axis and rejection of unwanted signals on another axis.

In these situations, the sensors are aligned in a similar manner with respect to the signal that they are sensing. In this case, the signals from the individual sensors are summed electronically to provide increased output and improved signal to noise ratio due to the summation and at least partial cancelling of random noise generated in each sensor.

FIGS. 2, 3A-B and 4A-B show a way to achieve cancellation of unwanted signals due to sensor movement while still allowing desired signal pickup.

Figure 2:
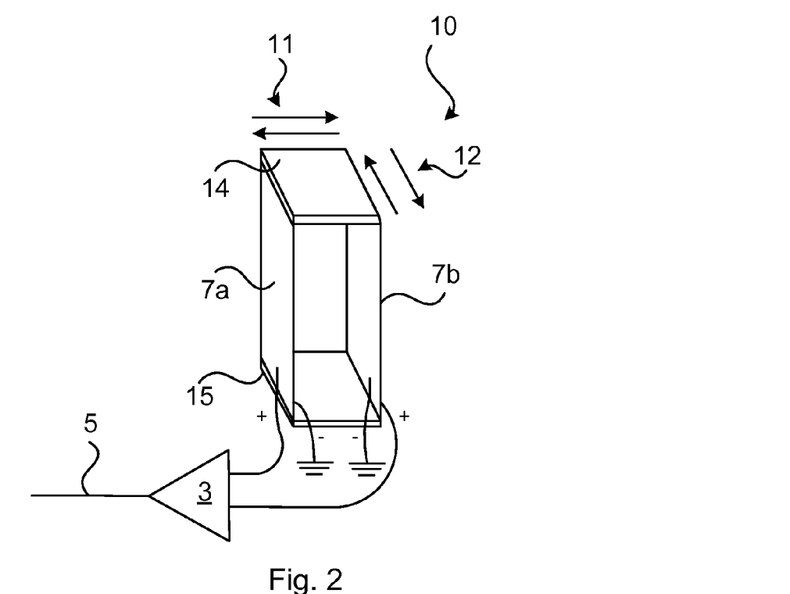
FIG. 2 is a schematic diagram illustrating a side view of one embodiment of a sensor.

FIG. 2 is a schematic diagram illustrates one embodiment of a sensor. A sensor 10 comprises a base piece 15 and a sensor plate 14. Between the base piece 15 and the sensor plate 14, there is a first pair of sensor membranes comprising a first sensor membrane 7a and a second sensor membrane 7b. The sensor signals output from the first sensor membrane 7a and the second sensor membrane 7b are summed in a combiner 3 such as a summing amplifier or any other suitable device which allows the two signals from the first sensor membrane 7a and the second sensor membrane 7b to be combined. Another terminal of each one of the sensor membranes 7a-b is a respective ground terminal (also known as the negative terminal). Due to the mechanical construction of this embodiment, there is a relatively low resistance to motion in a perpendicular direction if which is essentially perpendicular to the sensor membranes 7a-b. Conversely, there is a relatively high resistance to motion in a parallel direction 12, which is essentially parallel to the sensor membranes 7a-b.

Figure 3A:
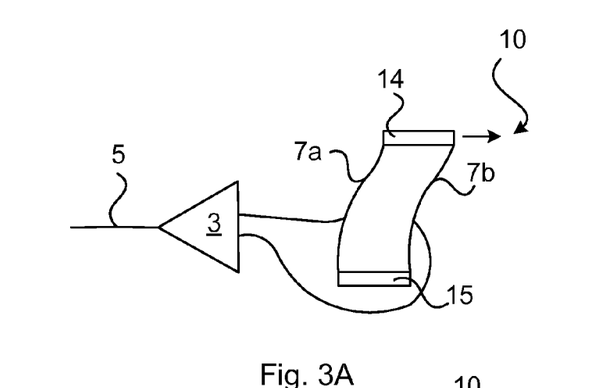
FIG. 3A is a schematic diagram illustrating a side view of when the sensor of FIG. 2 is skewed and FIG. 3B is a schematic graph illustrating resulting sensor signals.

FIG. 3A is a schematic diagram illustrating when the sensor to of FIG. 2 is skewed. The sensor membranes 7a-b are stiff but flexible piezoelectric film and flex mainly in one direction, as is illustrated in more detail below. The sensor membranes 7a-b here comprise piezoelectric film designed to give greatest electrical output when flexed in a direction perpendicular to the plane of film. Therefore, each sensor will give highest output in the direction that has low resistance to motion (see the perpendicular direction 11 of FIG. 2). Note that the piezoelectric films are oriented with opposite electrical polarity with respect to one another. In other words, their respective sides of positive electrical polarity face each other or face away from each other, which could also be expressed as their respective sides of negative electrical polarity face each other or face away from each other. The sensor membranes are arranged between (and optionally mounted to both of) the sensor plate 14 and a base piece 15, which e.g. can be mounted to a device collecting the signals from the sensor such as a stethoscope. The sensor plate 14 can be any essentially planar structure and may be curved, either concave or convex, or both.

Figure 3B:
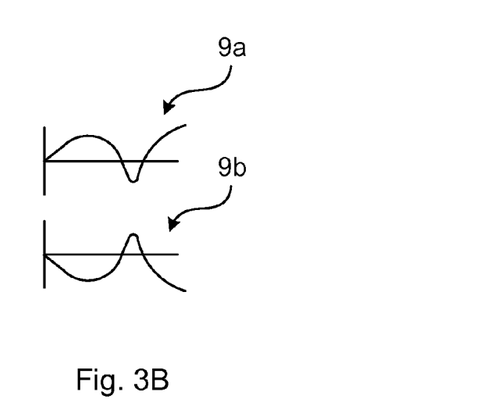

FIG. 3B illustrates sensor electrical outputs from the two respective sensor membranes 7a-b of FIG. 3A when the sensor plate 14 of the assembly is moved laterally in relation to the base piece 15. A first electrical signal 9a originates form the first sensor membrane 7a and a second electrical signal 9b originates from the second sensor membrane 7b. Due to the configuration of the sensor membranes being mounted with geometrically opposite polarities of the sides of the sensor membranes, the variation in electrical output resulting from the lateral movement is the same but with opposite polarity. When the first electrical signal 9a and the second electrical signal 9b are combined in the combiner 3, the effect from the lateral movement is thus essentially cancelled.

Figure 4A:
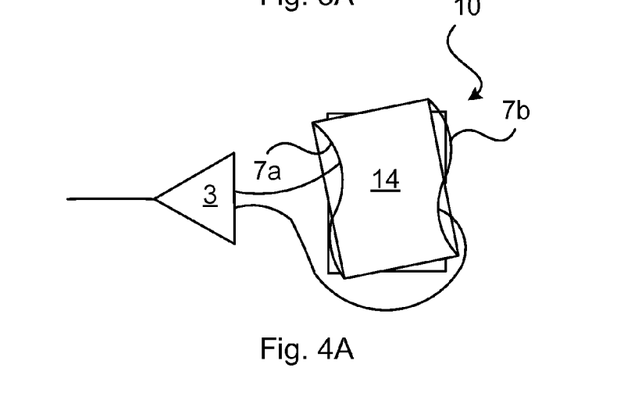
FIG. 4A is a schematic diagram illustrating a top view of when the sensor of FIG. 2 is twisted in relation to the base piece and FIG. 4B is a schematic graph illustrating resulting sensor signals.
Figure 4B:
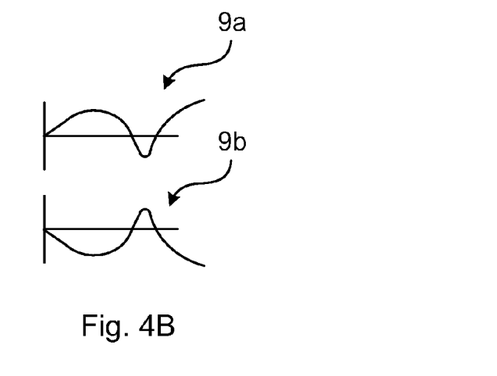

FIG. 4A illustrates a situation where the top of the assembly is twisted in relation to the base piece and FIG. 4B illustrates the corresponding electrical signals 9a-b. In analogy with the case illustrated in FIGS. 3A-B, opposite polarity electrical signal is generated by each of the sensor membranes 7a-b since their respective sides of positive electrical polarity face each other or face away from each other. Given that the sensors are similar within manufacturing tolerances and assembly is symmetrical, the signals generated by the sensors 7a-b should largely cancel out each other when summed.

Figure 5:
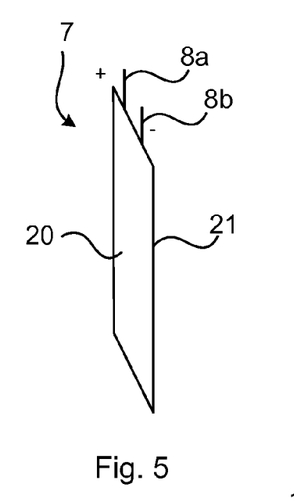
FIG. 5 is a schematic illustration of a sensor membrane used in FIGS. 2, 3A, 4A, and FIGS. 6-14.
Figure 6:
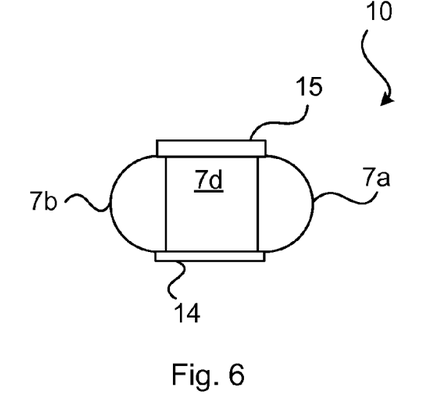
FIG. 6 is a schematic side view illustrating an embodiment being extension of the sensor shown in FIGS. 2, 3A and 4A, where four sensor membranes are employed.
Figure 7:
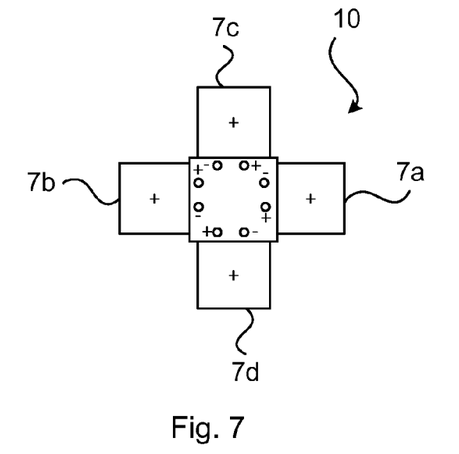
FIG. 7 is a schematic top view illustrating the sensor of FIG. 6.

FIGS. 5, 6 and 7 illustrate one embodiment.

FIG. 5 is a schematic illustration of a sensor membrane used in FIGS. 2, 3A, 4A, and FIGS. 6-14. All sensor membranes are here illustrated by a single sensor membrane 7. The sensor membrane 7 is sensitive to force and/or variations in force such as vibrations and can e.g. be a piezoelectric film sensor where two contact films form the surfaces of the sensor. One contact film on one face 20 is designated the positive terminal 8a and the other contact film 21 on the other face is designated the negative or ground terminal 8b. In other words, the sensor membrane 7 has a side of positive electrical polarity and a side of negative electrical polarity. The films are optionally protected by a covering overall film of plastic to give desired ruggedness and stiffness.

FIGS. 6 and 7 illustrate how four sensor membranes are employed in one embodiment. This comprises two pairs of sensors in polarity opposition. A first pair of sensor membranes comprise a first pair of sensor membranes comprise a first sensor membrane 7a and a second sensor membrane 7b. A second pair of sensor membranes comprise third sensor membrane 7c and a fourth sensor membrane 7d. This is most easily seen in FIG. 7, showing that the electrical polarity of all membranes 7a-d facing outwards is the same (positive in this example, but it could equally well be negative). Optionally, the polarity of the outward facing side of the first and second sensor membranes could be of one polarity and the outward facing side of the third and fourth sensor membranes could be of another polarity. The sensor membranes 7a-d are fixed at or close to the edges to the four sides of the sensor plate 14 and the base plate 15. The sensor plate 14 and the base plate 15 are here depicted in a square shape; however, these could be of any suitable shape, including circular, elliptical, rectangular, hexagonal, octagonal, etc. The fixing of the sensor membranes 7a-b is performed such that the angle of contact with the sensor plate 14 causes the sensors to bend. The shape is naturally formed when the bending force reaches equilibrium with stiffness of the membranes which tries to return the sensors to a flat position.

The shape of the sensor membranes 7a-b can be configured such that a planar movement of the sensor plate, in relation to the base piece, is more restricted in a first direction along the sensor plate compared to a second direction along the sensor plate. This can e.g. be effected by each one of the third sensor membrane and the fourth sensor membrane being longer than each one of the first sensor membrane and the second sensor membrane, measured along the respective sensor membrane between the sensor plate and the base piece.

The sensor membranes 7a-d of the sensor in FIGS. 6 and 7 are arranged in two cross-wise pairs, i.e. the shortest line between the first sensor membrane 7a and the second sensor membrane 7b is essentially perpendicular to the shortest line between the third sensor membrane 7c and the fourth sensor membrane 7d.

The base plate 15 is used for fixing the sensor assembly to a device or other structure, such as to a stethoscope. The sensor plate 14 is used for sensing forces perpendicular to the plate. These forces result in signals of the same polarity on opposing sensor membranes and are not cancelled out due to the opposing polarities of sensor membranes of the first and/or second pair of sensor membranes. The diagrams show square sensor plates 14 and base plates 15 and rectangular sensors 7a-d. In practice, the sensor plates 14 and base plates 15 may be of any shape. However to achieve good cancellation of unwanted signals, the sensor membranes of any pair are mirror images of each other (in terms of polarity) and the structure is symmetrical. The sensor plate may also implemented by a continuous outer film joining the sensor membranes.

Figure 8:
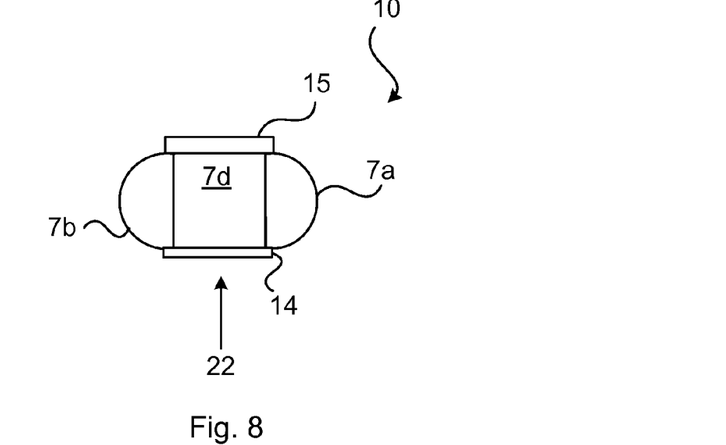
FIG. 8 is a schematic a side view of the sensor of FIG. 2, illustrating how forces are sensed by the sensor.
Figure 9:
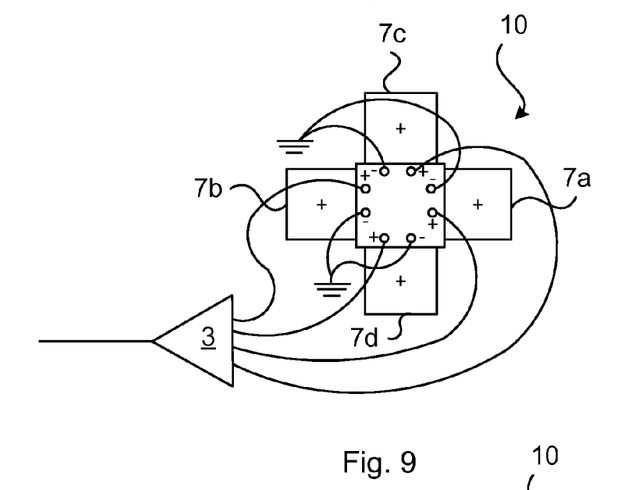
FIG. 9 is a schematic top view of the sensor of FIG. 8, also comprising a combiner.

FIG. 8 shows the application of the sensor to sensing forces 22 perpendicular to the sensing plate/ring (the preferred axis for signal pickup). The applied force deflects the sensor membranes 7a-d similarly and their outputs can be summed with a summing amplifier, as shown FIG. 9. This leads to increased signal output from the amplifier and at least partial cancellation of random electrical noise. From the illustration of FIGS. 3A-B and FIGS. 4A-B it can be seen that lateral forces or torsional twisting forces on the sensing plate/ring will cause electrical output that is essentially cancelled out when summed. Additionally pre-stress of the sensor membrane by bending gives increased sensitivity, leading to several advantages. Firstly, pick up of unwanted signals off axis to the desired direction of sensing is reduced. Secondly, sensitivity for the desired direction of sensing (represented by the arrow) is improved. The desired direction of sensing can be a direction which is perpendicular to the face of the sensor plate 14. Thirdly, the signal to noise ratio is improved.

In an alternative configuration the outputs of the sensors may be directly summed at one amplifier input leading to considerable simplification of electronics.

The size of the sensor assembly is scalable, limitations being the maximum and minimum membrane sizes that can be manufactured.

Figure 10:
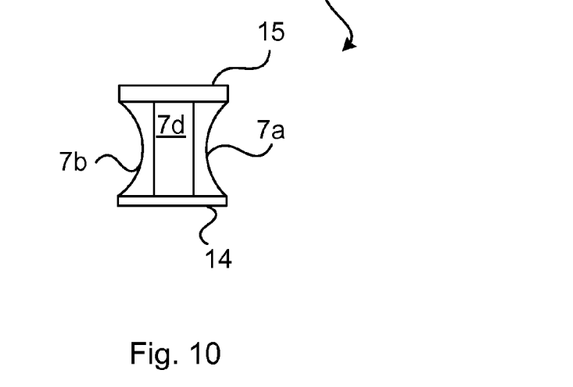
FIG. 10 is a schematic side view illustrating an embodiment being extension of the sensor shown in FIGS. 2, 3A and 4A, where four sensor membranes are employed.
Figure 11:
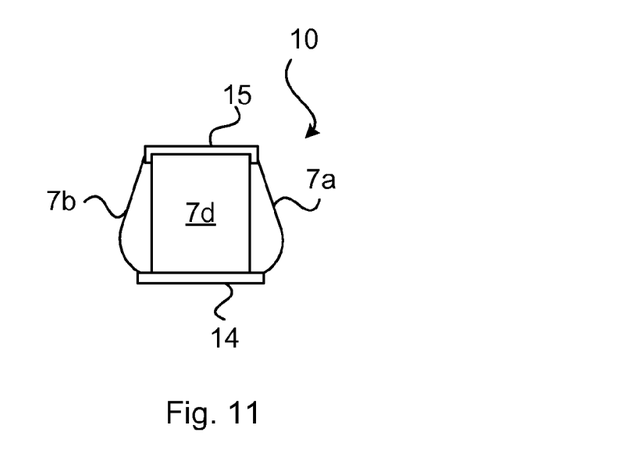
FIG. 11 is a schematic side view illustrating an embodiment being extension of the sensor shown in FIGS. 2, 3A and 4A, where four sensor membranes are employed.

FIG. 8 depicts one form of sensor arrangement that is suited for a sensor assembly of small depth. FIGS. 10 and 11 show two alternative arrangements which reduce the width requirements of the sensor. The first of these variations, FIG. 10 shows sensor membranes formed as narrower strips to allow bending to be encompassed within the dimensions of the plates. The second variant FIG. 11 changes the angle of membrane fixation on one plate/ring and is a compromise solution between the wider solution of FIG. 6 and the reduced width solution FIG. 10. The narrower the membrane strips become, the less stable the assembly becomes with regards to lateral motion, therefore the second variant, of the sensor 10 shown in FIG. 11 is better in this regard, whilst still achieving a reduction in overall width.

Figure 12:
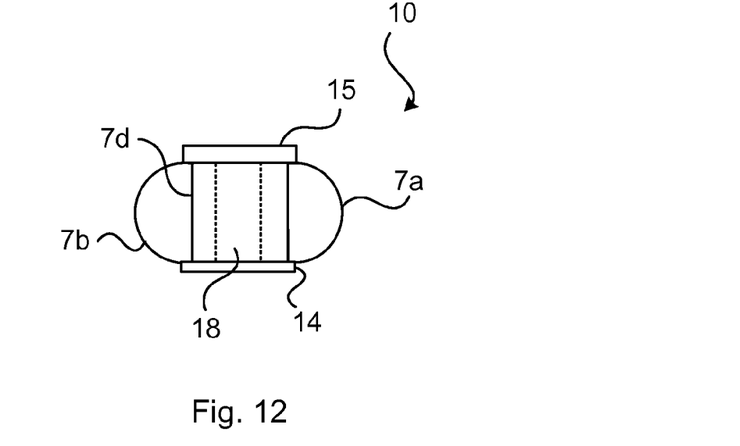
FIG. 12 is a schematic side view illustrating an embodiment being extension of the sensor shown in FIG. 8, also comprising a dampener.

The assembly of FIG. 8 exhibits spring-like behaviour when force is applied to the sensing plate/ring. Therefore the structure may have resonant properties, which in some cases are in a frequency range which makes them undesired. Control of resonance can be provided by the addition of a dampener 18 arranged between the base plate and the sensor plate, comprising material that can dampen resonance that joins the top and bottom plates/rings. The dampener 18 is depicted in FIG. 12 as a pillar for resonance control which could be a foam/rubber material or any other material that allows deflection whilst damping resonance. The dampener 18 can be any resilient material which provides a dampening of the motion of the sensor plate towards the base plate.

While the scheme of FIG. 12 provides effective resonance control, it reduces the final electrical output of the sensor assembly because the force required to deflect the structure is increased, e.g. in comparison with the embodiment shown in FIG. 8. The resonance control material needs to increase in stiffness as the requirement for resonance control increases.

Figure 13:
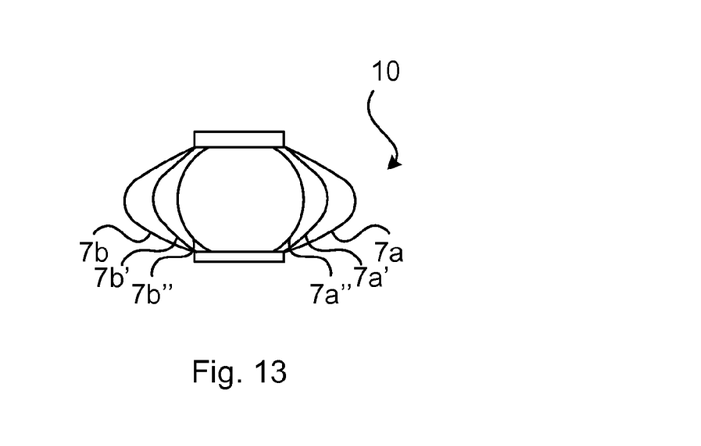
FIG. 13 is a schematic side view illustrating an embodiment being extension of the sensor shown in FIGS. 2, 3A and 4A, where six sensor membranes are employed.

FIG. 13 illustrates an embodiment of a sensor 10. In this example the sensor membranes are arranged in a configuration which is replicated concentrically to a point where all available space is utilized. In this example, there is a first pair of sensor membranes 7a, 7b, a second pair of sensor membranes 7a', 7b' and a third pair of sensor membranes 7a", 7b". Each additional sensor may exhibit different properties of stiffness, either by change of bending radius or membrane strength. The outputs of the additional sensors are fed to the electronic summing amplifier. By this method, resonance can be controlled because each additional sensor pair has a different resonance property to the others and therefore the sensor pairs will damp each other. Overall loss of electrical output is reduced because each additional pair of sensors creates extra signal which can be summed into final output, even though the structure is more rigid. Any suitable number of pairs can be employed. In one embodiment, four sensors are added for each concentric layer, with pairs opposing each other on the opposite sides of a rectangle.

In the sensor of FIG. 13, the sensor membranes are arranged in pairs which are gradually further away from the centre of the sensor, in a straight line. This can also be expressed, for the first four sensor membranes, such that the shortest line between the first sensor membrane 7a and the second sensor membrane 7b is essentially parallel to the shortest line between the third sensor membrane 7a' and the fourth sensor membrane 7b'. Taking into account the fifth sensor membrane 7a" and the sixth sensor membrane 7b", the shortest line between the fifth sensor membrane 7a" and the sixth sensor membrane 7b" is also essentially parallel to the shortest line between the third sensor membrane 7a' and the fourth sensor membrane 7b'. Essentially parallel can here be interpreted as a deviation of less than 30 degrees. In one embodiment, essentially parallel is to be interpreted as a deviation of less than 10 degrees.

Figure 14:
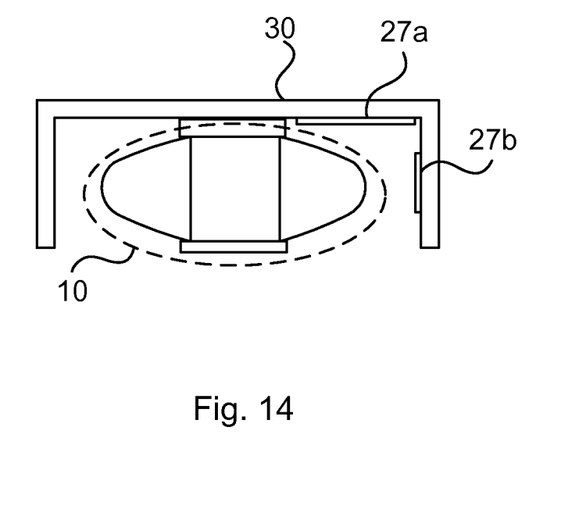
FIG. 14 is a schematic side view illustrating the sensor of FIGS. 2, 3A, 4A, and FIGS. 6-13 provided in a housing.

FIG. 14 is a schematic diagram illustrating a sensor 10 provided in a housing 30. The sensor 10 is here housed in a shell structure. The shell and sensor are placed in contact with a surface to capture its vibration profile. In this situation, unwanted signals may be generated by vibrations traveling through the shell into the surface in contact with the sensor. In this case additional sensors 27a-b are attached to the housing and their output is summed into the overall sensor output. These sensors 27a-b may be of the type shown in FIG. 5 or other contact sensor. The additional sensors 27a-b can be oriented to produce an inverse of the shell generated noise or an inverting amplifier can be used prior to summation so that the shell noise is cancelled.

The embodiments presented herein can be applied broadly just like the associated sensors. Its use extends to the medical environment for capture of lung, heart and bowel sounds such as in an electronic stethoscope. It can be used in industrial applications for general purpose vibration sensing. Although primarily intended as a contact sensor its sensitivity allows it to be used for wave pressure sensing in gas and fluid environments whilst retaining the enhanced directional properties.

Figure 15:
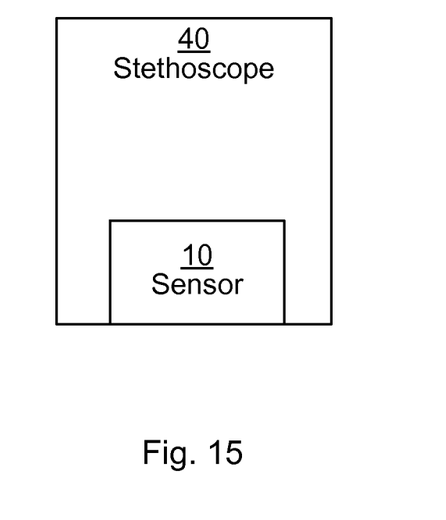
FIG. 15 is a schematic diagram illustrating a sensor of FIGS. 2, 3A, 4A, and FIGS. 6-13 forming part of an electronic stethoscope 40.

FIG. 15 is a schematic diagram illustrating a sensor 10 according to any of the embodiments described herein forming part of an electronic stethoscope 40. The stethoscope may comprise other components not shown here such as a speaker/headset, processor, filter, processor, etc.

Here now follows a list of enumerated embodiments.

I. A sensor comprising:
   a sensor plate;
   a base piece; and
   a first pair of sensor membranes, each connected between the sensor plate and the base piece, wherein the sensor membranes allow movement of the sensor plate in relation to the mounting piece.

II. The sensor according to embodiment I, further comprising a second pair of sensor membranes.

III. The sensor according to embodiment II, wherein the first and second pair of sensor membranes are arranged such that a planar movement of the sensor plate, in relation to the base piece, is more restricted in a first direction along the sensor plate compared to a second direction along the sensor plate.

IV. The sensor according to embodiment III, wherein the first pair of sensor membranes are longer than the second pair of sensor membranes, as measured between the sensor plate and the base piece, whereby the first pair of sensor membranes are curved more than the second pair of sensor membranes.

V. A stethoscope comprising a sensor according to any one of embodiments I to IV.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. A sensor comprising:
   a sensor plate;
   a base piece; and
   a first sensor membrane and a second sensor membrane, each having a side of positive electrical polarity and a side of negative electrical polarity;
   wherein each one of the first sensor membrane and the second sensor membrane is mounted between the sensor plate and the base piece while allowing movement of the sensor plate in a direction that is parallel to the base piece; and
   wherein the first sensor membrane and the second sensor membrane are mounted with opposing polarities such that their respective sides of positive electrical polarity face each other or face away from each other;
   a summing amplifier with a first input coupled to the first sensor membrane and a second input coupled to the second sensor membrane;
   whereby because of the opposing polarities of the first and second sensor membranes, when the sensor plate moves in the direction that is parallel to the base piece, signals generated by the first and second sensor membranes cancel each other out when combined by the summing amplifier, and when the sensor plate moves in a desired direction of sensing that is perpendicular to the sensing plate, the signals generated by the first and second sensor membranes are summed to produce an increased output from the summing amplifier.

2. The sensor according to claim 1, wherein each sensor membrane is a force sensitive membrane.

3. The sensor according to claim 1, wherein each sensor membrane is configured to generate a sensor signal bases on force components perpendicular to a plane of the sensor membrane along a side of the sensor membrane.

4. The sensor according to claim 1, further comprising a third sensor membrane and a fourth sensor membrane, each having a side of positive electrical polarity and a side of negative electrical polarity;
  wherein each one of the third sensor membrane and the fourth sensor membrane is mounted between the sensor plate and the base piece while allowing movement of the sensor plate in relation to the base piece; and
  the third sensor membrane and the fourth sensor membrane are mounted such that their respective sides of positive electrical polarity face each other or face away from each other.

5. The sensor according to claim 4, wherein the sensor membranes are arranged such that a planar movement of the sensor plate, in relation to the base piece, is more restricted in a first direction along the sensor plate compared to a second direction along the sensor plate.

6. The sensor according to claim 4, wherein each one of the third sensor membrane and the fourth sensor membrane are longer than each one of the first sensor membrane and the second sensor membrane, measured along the respective sensor membrane between the sensor plate and the base piece.

7. The sensor according to claim 4, wherein the shortest line between the first sensor membrane and the second sensor membrane is essentially perpendicular to the shortest line between the third sensor membrane and the fourth sensor membrane.

8. The sensor according to claim 4, wherein the shortest line between the first sensor membrane and the second sensor membrane is essentially parallel to the shortest line between the third sensor membrane and the fourth sensor membrane.

9. The sensor according to claim 8, further comprising a fifth sensor membrane and a sixth sensor membrane of the same type as the other sensor membranes, the fifth sensor membrane and sixth sensor membrane being mounted between the base piece and the sensor plate such that the shortest line between the fifth sensor membrane and the sixth sensor membrane is essentially parallel to the shortest line between the third sensor membrane and the fourth sensor membrane.

10. The sensor according to claim 8, wherein the first sensor membrane and the second sensor membrane has a first stiffness and the third sensor membrane and the fourth sensor membrane has a second stiffness which differs from the first stiffness.

11. The sensor according to claim 1, further comprising a combiner which combines signals from each one of the sensor membranes to a combined signal output.

12. The sensor according to claim 11, wherein the combiner is the summing amplifier.

13. The sensor according to claim 1, wherein each one of the sensor membranes comprises a piezoelectric film.

14. The sensor according to claim 1, further comprising a dampener arranged between the base piece and the sensor plate.

15. An electronic stethoscope comprising a sensor according to claim 1.

16. An electronic stethoscope comprising:
  a speaker;
  a processor;
  a filter; and
  a sensor, comprising:
    a sensor plate;
    a base piece; and
    a first sensor membrane and a second sensor membrane, each having a side of positive electrical polarity and a side of negative electrical polarity;
    a summing amplifier with a first input coupled to the first sensor membrane and a second input coupled to the second sensor membrane;
    wherein the base piece is mounted to the electronic stethoscope;
    wherein each one of the first sensor membrane and the second sensor membrane is mounted between the sensor plate and the base piece while allowing movement of the sensor plate in relation to the base piece; and
    wherein the first sensor membrane and the second sensor membrane are mounted with opposing polarities such that their respective sides of positive electrical polarity face each other or face away from each other;
    whereby because of the opposing polarities of the first and second sensor membranes, when the sensor plate moves in the direction that is parallel to the base piece, signals generated by the first and second sensor membranes cancel each other out when combined by the summing amplifier, and when the sensor plate moves in a desired direction of sensing that is perpendicular to the sensing plate, the signals generated by the first and second sensor membranes are summed to produce an increased output from the summing amplifier.

* * * * *